US00PP17196P3

(12) United States Plant Patent
Lim et al.

(10) Patent No.: US PP17,196 P3
(45) Date of Patent: Nov. 7, 2006

(54) SHRUB ROSE PLANT NAMED 'BAIIEF'

(50) Latin Name: *Rosa hybrida*
Varietal Denomination: BAIief

(75) Inventors: Peter P. Lim, Yamhill, OR (US); Martin Nemko, Oakland, CA (US)

(73) Assignee: Bailey Nurseries, Inc., St. Paul, MN (US)

( * ) Notice: Subject to any disclaimer, the term of this patent is extended or adjusted under 35 U.S.C. 154(b) by 41 days.

(21) Appl. No.: 11/004,920

(22) Filed: Dec. 7, 2004

(65) Prior Publication Data

US 2006/0123519 P1 Jun. 8, 2006

(51) Int. Cl.
*A01H 5/00* (2006.01)

(52) U.S. Cl. ..... Plt./107

(58) Field of Classification Search ..... Plt./107
See application file for complete search history.

*Primary Examiner*—Kent Bell
*Assistant Examiner*—June Hwu
(74) *Attorney, Agent, or Firm*—Buchanan Ingersoll PC

(57) ABSTRACT

A new and distinct variety of landscape shrub rose plant is provided which abundantly forms on a substantially continuous basis in clusters attractive double deep pink blossoms with a white eye. As the Blossoms mature, they fade to an attractive range of pale pink to hot pink. The blossoms also display a slight sweet rose fragrance. The plant exhibits a small, dense compact and bushy growth habit, attractive semi-glossy medium green foliage, and good tolerance to Black Spot and Powdery Mildew. The attractive medium green semi-glossy foliage contrasts nicely with the deep pink blossom coloration. The new variety is particularly well suited for growing as attractive ornamentation in parks and gardens. The plant performs well in front of a border, as a low hedge, or in a container.

2 Drawing Sheets

Botanical commercial classification: *Rosa hybrida*/Shrub Rose Plant.
Varietal denomination: 'BAIief'.

SUMMARY OF THE INVENTION

The new variety of *Rosa hybrida* landscape shrub rose plant was created at Yamhill, Oreg., U.S.A., during 1997 by artificial pollination wherein two parents were crossed which previously had been studied in the hope that they would contribute the desired characteristics. The female parent (i.e., the seed parent) was the Miniature 'TRObwich' variety (non-patented in the United States). The 'TRObwich' variety sometimes is known as the 'Simon Robinson' variety. The male parent (i.e., the pollen parent) was the Miniature 'JACcasp' variety (U.S. Plant Pat. No. 8,719). The 'JACcasp' variety sometimes is known as the 'Happy Trails' variety. The parentage of the new variety can be summarized as follows:

'TRObwich'×'Happy Trails'.

The seeds resulting from the above pollination were sown and plants were obtained which were physically and biologically different from each other. Selective study resulted in the identification during 1999 of a single plant of the new variety having the distinctive ornamental characteristics hereafter described.

It was found that the new variety of the present invention:

(a) exhibits a compact and bushy growth habit, (b) forms a substantially continuous basis in clusters attractive double deep pink blossoms with a white eye, (c) forms attractive semi-glossy medium green foliage, (d) is highly tolerant to Black Spot and Powdery Mildew, and (e) is particularly well suited for growing as attractive ornamentation in parks and gardens.

As the blossoms mature, they fade to an attractive range of pale pink to hot pink.

The new variety well meets the needs of the horticultural industry and can be grown to advantage in the landscape where attractive ornamentation is desired. The pink blossoms contrast nicely with the semi-glossy medium green foliage. The plant grows well in front of a border, as a low hedge, or in a container. An attractive new shrub rose that can be grown in U.S.D.A. Hardiness Zone Nos. 4 to 9 is provided.

The new variety can be readily distinguished from other varieties including its ancestors. For instance, the 'TRObwich' variety forms medium pink blossoms having a diameter of approximately 3 cm that possess 5 petals, and the 'JACcasp' variety forms medium pink very double blossoms having a diameter of approximately 4 cm and forms glossy dark green foliage. The blossoms are much like those of 'The Fairy' variety (non-patented in the United States) except the color is deep pink and an attractive white eye is present.

The new variety beginning in August 1998 has been found to undergo asexual propagation by budding on an understock and by the rooting of cuttings. 'Dr. Huey' rootstock was used during the budding. Such asexual propagation by these techniques at Yamhill, Oreg., U.S.A., St. Paul, Minn., U.S.A., and at Phoenix, Ariz., U.S.A., has shown that the characteristics of the new variety are stable and are strictly transmissible by such asexual propagation from one generation to another. Accordingly, the new variety reproduces true to type. The new variety grows well on its own roots.

Initially the new plant was designated 97K-100. The new plant has been named the 'BAIief' variety, and currently is being marketed while using the GARDEN PATH, LITTLE MISCHIEF, and EASY ELEGANCE trademarks.

BRIEF DESCRIPTION OF THE PHOTOGRAPHS

The accompanying photographs show as nearly true as it is reasonably possible to make the same in color illustrations of this character, typical specimens of the new variety. The rose plants of the new variety had been propagated by the rooting of cuttings, were approximately two and three years of age, and were being grown outdoors during the 2003 and 2004 seasons at St. Paul, Minn., U.S.A., and at Yamhill, Oreg., U.S.A.

DETAILED DESCRIPTION

Figure 1:
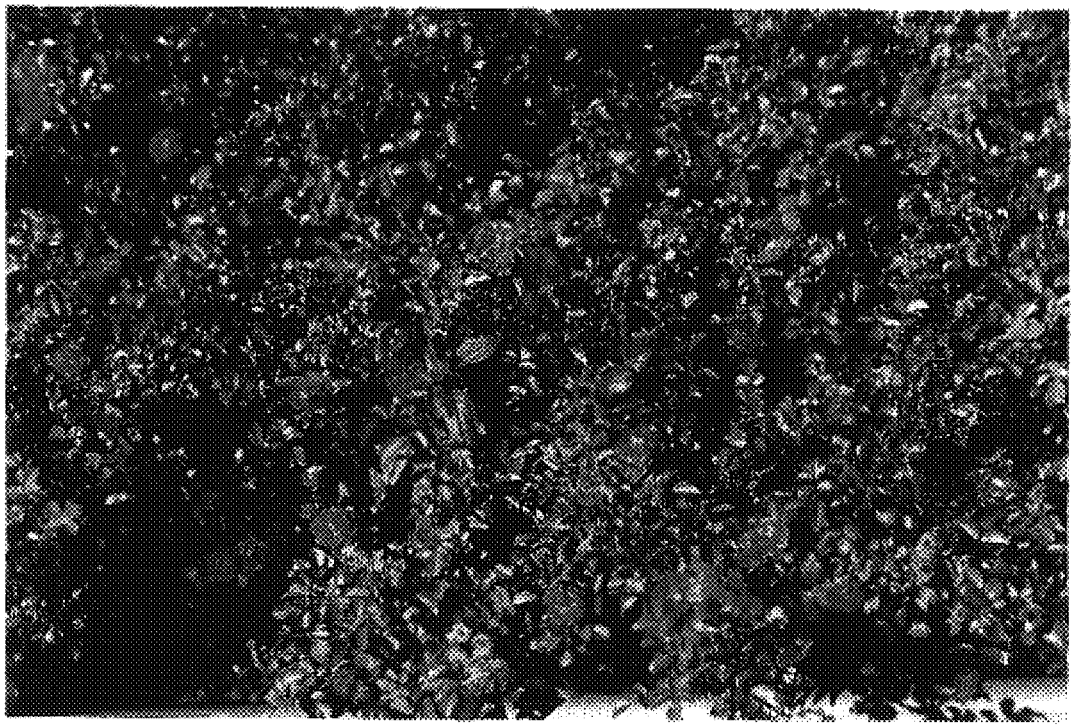
FIG. 1 illustrates from a distance a mass of typical plants of the new variety wherein the pink blossoms with a white eye and dense medium green foliage are shown.
Figure 2:
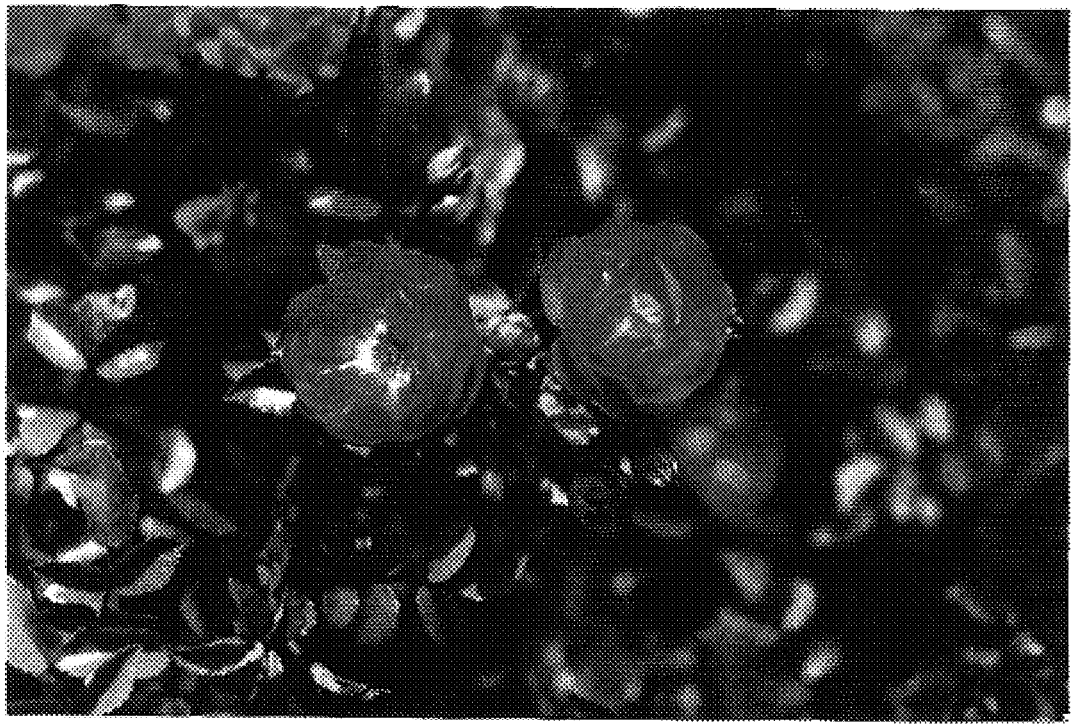
FIG. 2 illustrates a closer view of typical blossoms and foliage of the new variety.
Figure 3:
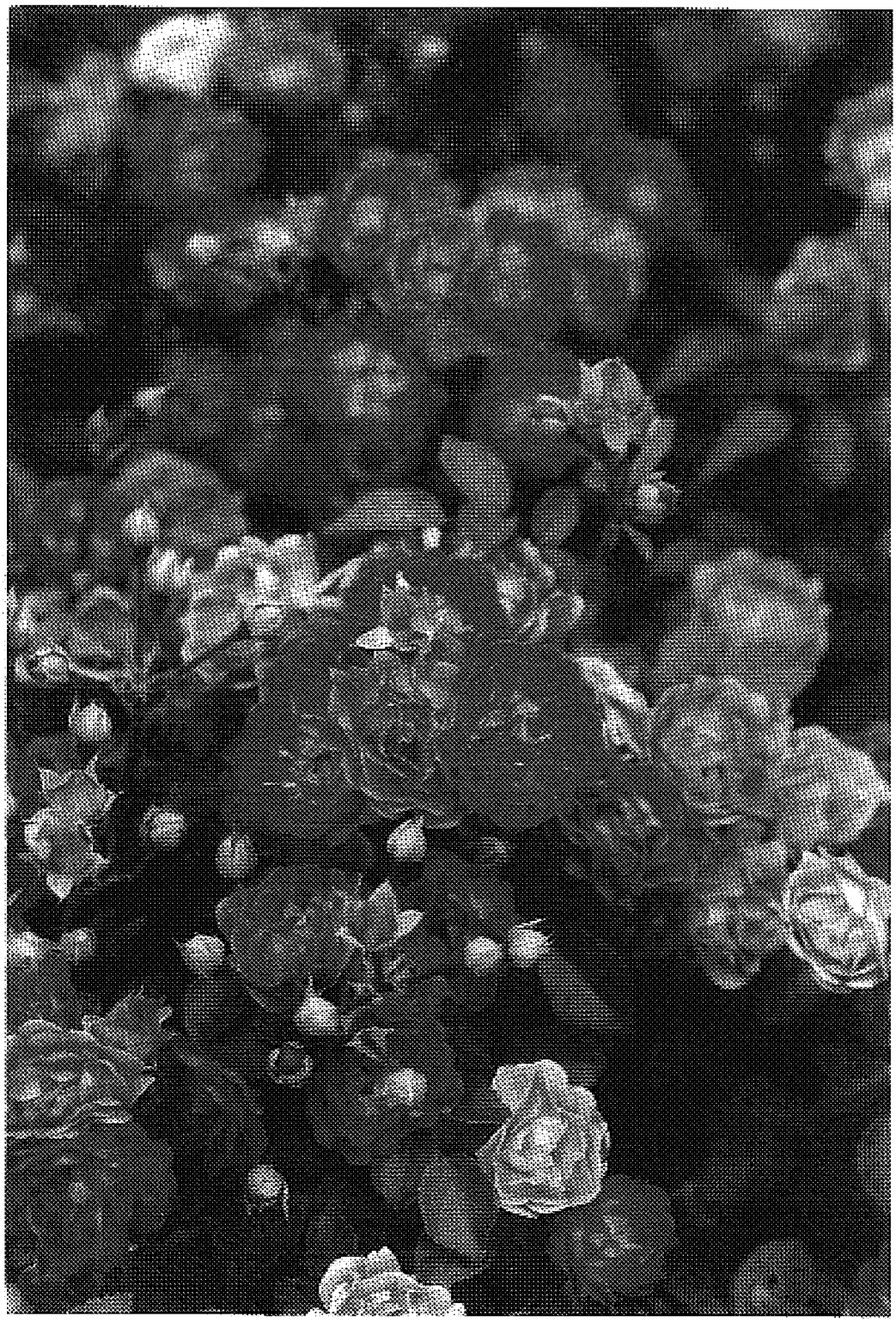
FIG. 3 illustrates an additional view of the typical pink blossoms of the new variety at various stages of maturity as well as the foliage.

The chart used in the identification of the colors is that of The Royal Horticultural Society (R.H.S. Colour Chart). Common color terms are to be accorded their ordinary dictionary significance. The description is based on the observation of two, three and four year-old plants while grown outdoors on their own roots during June 2003, at Yamhill Oreg., U.S.A., and during July 2004 at St. Paul, Minn., U.S.A.

Botanical classification: *Rosa hybrida,* 'BAIief'.
Class: Landscape Shrub.
Plant:
- *Height.*—Approximately 50 to 60 cm at the end of the growing season.
- *Width.*—Approximately 60 cm on average at the end of the growing season.
- *Habit.*—Rounded, compact and bushy.

Branches:
- *Color.*—Young stems: Yellow-Green Group 144A suffused with Greyed-Purple Group 187A and 187B. Adult wood: Yellow-Green Group 146B with streaks of Greyed-Green Group 197A.
- *Thorns.*—Size: approximately 0.3 cm in length on average. Shape: generally triangular to slightly hooked. Quantity: approximately 8 on average over a length of 5 cm. Color: Red-Purple Group 59B and 59C when mature.
- *Texture.*—Young stem: semi-glossy with sparse tiny thorns. Adult wood: glabrous with bark-like ridges.

Leaves:
- *Stipules.*—Generally parallel with the auricle facing outward, approximately 1.4 cm in length on average, approximately 5 mm in width on average, and the coloration is Green Group 143C with some Yellow Green on ridges on either side of the center.
- *Auricles.*—Size: approximately 4 mm in length on average, and approximately 2 mm in width on average. Shape: generally triangular with foliaceous appendages of approximately 2 mm on the margin. Color: commonly between Green Group 137B and 137C.
- *Petioles.*—Upper surface: Green Group 143A in coloration, glabrous and somewhat flat with a central valley. Under surface: Yellow-Green Group 144B in coloration, and bears some small prickles of approximately 1 mm in length. Length: commonly approximately 1.4 cm on average. Diameter: commonly approximately 1.2 mm on average.
- *Size.*—Length: commonly approximately 8.5 cm for a five-leaflet leaf. Width: commonly approximately 4.5 cm for a five-leaflet leaf.
- *Leaflets.*—Number: 3, 5 (most often), and 7. Shape: generally obovate to elliptic with a rounded base and an acuminate tip. Margin: serrulate. Texture: bears a semi-glossy finish. Length: approximately 2.0 to 2.75 cm on average. Width: approximately 1.25 to 1.75 cm on average. General appearance: medium green with a semi-glossy surface when mature. Color (young foliage): Upper surface: Yellow-Green Group 146A and 146B commonly with a lighter central valley of Green Group 138C. Under surface: Yellow-Green Group 146C. Color (adult foliage): Upper surface: Yellow-Green Group 146A and 146B with a lighter central valley of Green Group 138C. Under surface: Yellow-Green Group 146C.

Inflorescence:
- *Number of flowers.*—Commonly approximately 28 blooms on average in a cluster per lateral stem.
- *Peduncle.*—Glabrous, relatively stiff, approximately 2.4 cm in length on average, approximately 1.5 mm in diameter on average, and between Yellow-Green Group 144B and 144C suffused with Red-Purple Group 59A on the upper side and commonly covered with prickles of Red-Purple Group 59A on the under side.
- *Sepals.*—Upper surface: commonly near Yellow-Green Group 144B suffused with Green Group 143A, and tomentose. Under surface: Green Group 143A and lightening to Green Group 145B at the margin. Size: approximately 1.25 cm in length. Apex: apiculate and expands to a leaf shape with a main vein on the three outer sepals, and pointed on the two inner sepals. Foliaceous appendages: commonly present on the three outer sepals with one or two appendages per side, approximately 1.3 mm in length on average with a pointed apex and a ciliate margin, and the two inner sepals commonly possess only a ciliate margin and a pointed apex.
- *Buds.*—Shape: globose. Size: small. Length: approximately 2 cm on average. Diameter: approximately 1.75 cm on average. Color: Upper petal surface: Red-Purple Group 60C. Under petal surface: Red-Purple Group 60B.
- *Flower.*—Arrangement: in a cluster or compound panicle. Diameter: approximately 2.5 cm on average. Form: double. Color (when opening begins): Upper surface: Red-Purple Group 57A blending with Red-Purple Group 64C and 64D, and White Group 155B toward the basal petal spot. Under surface: Red-Purple Group 57D blended with Red-Purple Group 57A at the margin. Color (when blooming): Upper surface: Red-Purple Group 66A blending with Red-Purple Group 67B and White Group 155D toward the basal petal spot. Under surface: between Red-Purple Group 66C and 66D. Color (at end of blooming): Upper surface: Red-Purple Group 67D blending with Red-Purple Group 65A and 65B and with White Group 155D toward the basal petal spot. Under surface: Red-Purple Group 65A blended with Red-Purple Group 68A and 68B. Color (basal petal spot): Yellow Group 2D. Fragrance: slight sweet rose. Lasting quality: the blossoms commonly last approximately 4 to 7 days on average depending upon the temperature and sunlight exposure. Petal number: commonly approximately 19 to 24 on average under normal growing conditions. Petal size: approximately 1.3 cm in length on average and approximately 0.9 cm in width on average. Petal shape: generally heart-shaped. Petal texture: glabrous, smooth, and satiny. Petal drop: commonly the petals detach cleanly at full blossom maturity and do not detract from other young blooms. Anthers: Yellow-Orange Group 17A in coloration. Anther size: approximately 1.2 mm in length on average and approximately 0.9 mm in width on average. Filament number: commonly approximately 37 on average. Filament size: approximately 4.2 mm in length on average and approximately 0.7 mm in width on average. Filament color: Yellow-Green Group 145B. Pistils: approximately 15 on average, and are separate and free. Stigmas: Yellow-Green Group 151A in coloration. Stigma size: approximately 0.9 mm in length on average and approximately 0.6 mm in width on average. Styles: Yellow-Green Group 154B in coloration. Style size: approximately 5.4 mm in length on average and approximately 0.9 mm in width on average. Receptacle: urn-shaped, glabrose, at bud break approximately 5 mm in length on average and approximately 4.3 mm in width on average, and Yellow-Green Group 144A in coloration with Greyed-Purple Group 183B on the side exposed to the sun. Hips: obovate in configuration, approximately 1 cm in length and approximately 8 mm in width. No hips are available for further characterization. Seeds: medium beige in coloration and approximately 3 mm in length.

Development:

*Vegetation.*—Vigorous, compact and dense.

*Blooming.*—Substantially continuous, everblooming.

*Resistance to diseases.*—Highly tolerant to Black Spot, and Powdery Mildew.

*Hardiness zone.*—U.S.D.A. Hardiness Zone Nos. 4 to 9.

What is claimed is:

1. A new and distinct variety of landscape shrub rose plant characterized by the following combination of characteristics:

(a) exhibits a compact and bushy growth habit, (b) forms on a substantially continuous basis in clusters attractive double deep pink blossoms with a white eye, (c) forms attractive semi-glossy medium green foliage, (d) is highly tolerant to Black Spot and Powdery Mildew, and (e) is particularly well suited for growing as attractive ornamentation in parks and gardens;

substantially as herein shown and described.

* * * * *